United States Patent
Manzo (10) Patent No.: US 8,349,019 B2
(45) Date of Patent: *Jan. 8, 2013

(54) METHOD AND APPARATUS FOR ANASTOMOSIS INCLUDING ANNULAR JOINING MEMBER

(75) Inventor: Scott Manzo, Shelton, CT (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/312,259

(22) Filed: Dec. 6, 2011

(65) Prior Publication Data

US 2012/0078276 A1    Mar. 29, 2012

Related U.S. Application Data

(63) Continuation of application No. 10/516,437, filed as application No. PCT/US03/11661 on Apr. 16, 2003, now Pat. No. 8,083,804.

(60) Provisional application No. 60/390,103, filed on Jun. 19, 2002.

(51) Int. Cl.
*A61F 2/04* (2006.01)

(52) U.S. Cl. ............ 623/23.66; 606/153; 606/154

(58) Field of Classification Search ........... 606/153–156
See application file for complete search history.

(56) References Cited

U.S. PATENT DOCUMENTS

| | | | |
|---|---|---|---|
| 1,390,564 A | 9/1921 | Knorr | |
| 2,127,903 A | 8/1938 | Bowen | |
| 3,254,650 A | 6/1966 | Collito | |
| 4,334,551 A | 6/1982 | Pfister | |
| 4,366,819 A | 1/1983 | Kaster | |
| 4,553,543 A | 11/1985 | Amarasinghe | |
| 4,598,712 A * | 7/1986 | Rebuffat et al. | 606/153 |
| 4,803,984 A | 2/1989 | Narayanan et al. | |
| 4,848,367 A | 7/1989 | Avant et al. | |
| 4,911,164 A | 3/1990 | Roth | |
| 4,931,057 A | 6/1990 | Cummings et al. | |
| 4,957,499 A | 9/1990 | Lipatov et al. | |
| 5,047,039 A | 9/1991 | Avant et al. | |
| 5,122,156 A | 6/1992 | Granger et al. | |
| 5,234,448 A | 8/1993 | Wholey et al. | |
| 5,403,333 A | 4/1995 | Kaster et al. | |
| 5,411,508 A | 5/1995 | Bessler et al. | |
| 5,425,739 A | 6/1995 | Jessen | |

(Continued)

FOREIGN PATENT DOCUMENTS

WO    WO 03/088848    10/2003

(Continued)

OTHER PUBLICATIONS

U.S. Appl. No. 10/514,140, entitled "Method and Apparatus for Radical Prostatectomy Anastomosis" filed Nov. 9, 2004.

(Continued)

*Primary Examiner* — Ryan Severson
*Assistant Examiner* — David Eastwood (57) ABSTRACT

Apparatus and method for performing surgical anastomotic procedures are disclosed herein. The apparatus for performing the surgical anastomotic procedure includes a tubular sleeve defining an axial lumen therethrough, a positioning tube defining an axial lumen therethrough, an expansion assembly having a tubular body and an expandable tip operatively coupled to a distal end thereof, and an anchoring assembly. The positioning tube is preferably configured and adapted to be slidably received within the axial lumen of the tubular sleeve.

24 Claims, 5 Drawing Sheets

U.S. PATENT DOCUMENTS

| | | | |
|---|---|---|---|
| 5,464,414 A | 11/1995 | Cziffer | |
| 5,464,415 A | 11/1995 | Chen | |
| 5,478,353 A | 12/1995 | Yoon | |
| 5,486,187 A | 1/1996 | Schenck | |
| 5,540,701 A | 7/1996 | Sharkey et al. | |
| 5,545,171 A | 8/1996 | Sharkey et al. | |
| 5,549,619 A | 8/1996 | Peters et al. | |
| 5,554,162 A | 9/1996 | DeLange | |
| 5,569,272 A | 10/1996 | Reed et al. | |
| 5,578,044 A | 11/1996 | Gordon et al. | |
| 5,591,179 A | 1/1997 | Edelstein | |
| 5,591,206 A | 1/1997 | Moufarrège | |
| 5,674,231 A | 10/1997 | Green et al. | |
| 5,695,504 A | 12/1997 | Gifford, III et al. | |
| 5,700,272 A | 12/1997 | Gordon et al. | |
| 5,702,412 A | 12/1997 | Popov et al. | |
| 5,707,380 A | 1/1998 | Hinchliffe et al. | |
| 5,713,889 A | 2/1998 | Chang | |
| 5,713,903 A * | 2/1998 | Sander et al. | 606/326 |
| 5,716,370 A | 2/1998 | Williamson, IV et al. | |
| 5,741,277 A | 4/1998 | Gordon et al. | |
| 5,797,934 A | 8/1998 | Rygaard | |
| 5,814,005 A | 9/1998 | Barra et al. | |
| 5,817,113 A | 10/1998 | Gifford, III et al. | |
| 5,833,698 A | 11/1998 | Hinchliffe et al. | |
| 5,868,762 A | 2/1999 | Cragg et al. | |
| 5,904,697 A | 5/1999 | Gifford, III et al. | |
| 5,944,730 A | 8/1999 | Nobles et al. | |
| 5,951,576 A | 9/1999 | Wakabayashi | |
| 5,980,483 A | 11/1999 | Dimitri | |
| 6,024,748 A | 2/2000 | Manzo et al. | |
| 6,048,351 A | 4/2000 | Gordon et al. | |
| 6,051,007 A | 4/2000 | Hogendijk et al. | |
| 6,063,114 A | 5/2000 | Nash et al. | |
| 6,080,167 A | 6/2000 | Lyell | |
| 6,096,051 A | 8/2000 | Kortenbach et al. | |
| 6,149,658 A | 11/2000 | Gardiner et al. | |
| 6,152,937 A | 11/2000 | Peterson et al. | |
| 6,171,319 B1 | 1/2001 | Nobles et al. | |
| 6,171,321 B1 | 1/2001 | Gifford, III et al. | |
| 6,176,864 B1 | 1/2001 | Chapman | |
| 6,203,553 B1 | 3/2001 | Robertson et al. | |
| 6,206,913 B1 | 3/2001 | Yencho et al. | |
| 6,241,742 B1 | 6/2001 | Spence et al. | |
| 6,254,617 B1 | 7/2001 | Spence et al. | |
| 6,280,460 B1 | 8/2001 | Bolduc et al. | |
| 6,346,074 B1 | 2/2002 | Roth | |
| 6,350,280 B1 | 2/2002 | Nash et al. | |
| 6,371,965 B2 | 4/2002 | Gifford et al. | |
| 6,409,739 B1 | 6/2002 | Nobles et al. | |
| 6,428,550 B1 | 8/2002 | Vargas et al. | |
| 6,428,555 B1 | 8/2002 | Koster, Jr. | |
| 6,461,320 B1 | 10/2002 | Yencho et al. | |
| 6,488,692 B1 | 12/2002 | Spence et al. | |
| 6,508,252 B1 | 1/2003 | Berg et al. | |
| 6,533,812 B2 | 3/2003 | Swanson et al. | |
| 6,537,288 B2 | 3/2003 | Vargas et al. | |
| 6,558,429 B2 | 5/2003 | Taylor | |
| 6,569,173 B1 | 5/2003 | Blatter et al. | |
| 6,602,263 B1 | 8/2003 | Swanson et al. | |
| 6,616,675 B1 | 9/2003 | Evard et al. | |
| 6,620,176 B1 | 9/2003 | Peterson et al. | |
| 6,623,494 B1 | 9/2003 | Blatter | |
| 6,623,510 B2 | 9/2003 | Carley et al. | |
| 6,629,988 B2 | 10/2003 | Weadock | |
| 6,632,229 B1 | 10/2003 | Yamanouchi | |
| 6,635,066 B2 | 10/2003 | Tanner et al. | |
| 6,666,873 B1 | 12/2003 | Cassell | |
| 6,676,678 B2 | 1/2004 | Gifford et al. | |
| 6,682,540 B1 | 1/2004 | Sancoff et al. | |
| 6,695,859 B1 | 2/2004 | Golden et al. | |
| 6,695,867 B2 | 2/2004 | Ginn et al. | |
| 6,699,256 B1 | 3/2004 | Logan et al. | |
| 6,726,694 B2 | 4/2004 | Blatter et al. | |
| 6,736,825 B2 | 5/2004 | Blatter et al. | |
| 6,796,586 B2 | 9/2004 | Werth | |
| 6,800,081 B2 | 10/2004 | Parodi | |
| 6,802,847 B1 | 10/2004 | Carson et al. | |
| 6,830,584 B1 | 12/2004 | Seguin | |
| 6,866,674 B2 | 3/2005 | Galdonik et al. | |
| 6,884,250 B2 | 4/2005 | Monassevitch et al. | |
| 6,920,882 B2 | 7/2005 | Berg et al. | |
| 6,939,361 B1 | 9/2005 | Kleshinski | |
| 6,960,219 B2 | 11/2005 | Grudem et al. | |
| 6,984,238 B2 | 1/2006 | Gifford et al. | |
| 7,001,398 B2 | 2/2006 | Carley et al. | |
| 7,004,949 B2 | 2/2006 | Yencho et al. | |
| 7,018,387 B2 | 3/2006 | Suyker et al. | |
| 7,022,127 B2 | 4/2006 | Suyker et al. | |
| 7,041,110 B2 | 5/2006 | Yencho et al. | |
| 7,060,084 B1 | 6/2006 | Loshakove et al. | |
| 7,074,203 B1 * | 7/2006 | Johanson et al. | 602/72 |
| 7,094,248 B2 | 8/2006 | Bachinski et al. | |
| 7,104,949 B2 | 9/2006 | Anderson et al. | |
| 7,112,212 B2 | 9/2006 | Raza | |
| 7,115,136 B2 | 10/2006 | Park et al. | |
| 7,128,749 B1 | 10/2006 | Vargas et al. | |
| 7,131,959 B2 | 11/2006 | Blatter et al. | |
| 7,160,311 B2 | 1/2007 | Blatter et al. | |
| 7,182,771 B1 | 2/2007 | Houser et al. | |
| 7,232,449 B2 | 6/2007 | Sharkawy et al. | |
| 7,241,300 B2 | 7/2007 | Sharkawy et al. | |
| 7,267,680 B2 | 9/2007 | Wright | |
| 7,285,125 B2 | 10/2007 | Viola | |
| 7,303,569 B2 | 12/2007 | Yencho et al. | |
| 7,309,341 B2 | 12/2007 | Ortiz et al. | |
| 7,314,480 B2 | 1/2008 | Eidenschink et al. | |
| 7,320,692 B1 | 1/2008 | Bender et al. | |
| 7,331,613 B2 | 2/2008 | Schulte | |
| 7,351,247 B2 | 4/2008 | Kupiecki et al. | |
| 2002/0082614 A1 | 6/2002 | Logan et al. | |
| 2004/0111056 A1 | 6/2004 | Weststrate et al. | |
| 2004/0127854 A1 | 7/2004 | Leinsing et al. | |
| 2005/0033371 A1 | 2/2005 | Sommer et al. | |
| 2005/0165378 A1 | 7/2005 | Heinrich et al. | |
| 2005/0165432 A1 | 7/2005 | Heinrich | |
| 2005/0171563 A1 | 8/2005 | Heinrich et al. | |
| 2005/0171564 A1 | 8/2005 | Manzo | |
| 2005/0228411 A1 | 10/2005 | Manzo | |
| 2006/0200177 A1 | 9/2006 | Manzo | |

FOREIGN PATENT DOCUMENTS

| | | |
|---|---|---|
| WO | WO 2004/000093 | 12/2003 |
| WO | WO 2004/000134 | 12/2003 |
| WO | WO 2004/000135 | 12/2003 |
| WO | WO 2004/000136 | 12/2003 |
| WO | WO 2004/098418 | 11/2004 |

OTHER PUBLICATIONS

U.S. Appl. No. 10/517,404, entitled "Method and Apparatus for Anastomosis Including an Anchoring Sleeve", tiled Dec. 7, 2004.

U.S. Appl. No. 10/518,040, entitled "Method and Apparatus for Anastomosis Including Annular Adjoining Member", filed Dec. 9, 2004.

U.S. Appl. No. 10/514,774, entitled Method and Apparatus for Anastomosis Including an Anchoring Sleeve, filed Nov. 17, 2004.

U.S. Appl. No. 10/516,434, entitled "Method and Apparatus for Anastomosis", filed Nov. 30, 2004.

* cited by examiner

METHOD AND APPARATUS FOR ANASTOMOSIS INCLUDING ANNULAR JOINING MEMBER

CROSS-REFERENCE TO RELATED APPLICATIONS

This application is a continuation of U.S. application Ser. No. 10/516,437 filed Nov. 30, 2004, now U.S. Pat. No. 8,083,804, which is a National Stage Application of PCT/US03/11661 filed Apr. 16, 2003 under 35USC §371 (a), which claims benefit of U.S. Provisional Application No. 60/390,103 filed Jun. 19, 2002, and the disclosures of each of the above-identified applications are hereby incorporated by reference in their entirety.

BACKGROUND

1. Technical Field

The present disclosure relates to apparatus and methods for anastomosing two hollow body parts and, more particularly to apparatus and methods for anastomosing a urethral stump of a patient to the bladder following a radical prostatectomy.

2. Background of Related Art

Anastomosis is the bringing together and/or joining of two hollow of tubular structures. Most body conduits are generally cylindrical in configuration and have a circular cross-section. When it is desired to suture such a conduit, typically for attachment to another body conduit, sutures are placed around the circumference of the conduit in order to maintain the patency of its lumen or channel. This type of attachment is commonly referred to as an anastomosis. It can be appreciated that the sutures made on top of the conduit (i.e., on the side facing the surgeon) in an anastomosis are made relatively more easily than the sutures made underneath the conduit (i.e., on the side facing away from the surgeon).

The complexity of anastomosis attachment is made manifestly apparent in a surgical procedure referred to generally as a radical prostatectomy (i.e., a well established surgical procedure for patients with localized prostatic carcinoma). In general, radical prostatectomy procedures require the removal of cancerous tissue while preserving sexual function and continence in the patient. There are two primary types of radical prostatectomy approaches for the removal of prostate cancer, the retropubic approach and the perineal approach.

In the retropubic approach, a long up-and-down incision is made in the midline of the abdomen from the navel to the pubic bone. After the lymph nodes have been removed for study by the pathologist and a determination has been made to proceed with the removal of the prostate gland, the space underneath the pubic bone is cleaned and dissected and the removal of the entire prostate gland is generally begun at the end that is farthest from the bladder, i.e., next to the external urethral sphincter. Next, the prostatic urethra is divided, the prostatic urethra and the prostate gland through which it goes are then pulled upwards toward the bladder while the dissection continues behind the prostate gland, separating it from the layer of tissue that is connected to the rectum on its other side. As the dissection continues between the prostate and the rectum, the seminal vesicles, which are behind the base of the bladder will be removed along with the prostate gland. Once the seminal vesicles are free, the entire prostate gland and the seminal vesicles are removed. The bladder neck is then stitched closed to a small enough diameter so that it is about the same size as the stump of the urethra from which the prostate was detached. The bladder neck is then pulled down into the pelvis and positioned against the urethral stump and stitched thereto. This stitching is done typically around a Foley catheter which has been inserted through the penis all the way into the bladder.

In the perineal approach, an inverted "U" shaped incision is made going right over the anus, with the center of the "U" about three centimeters above the margin of the anus. The prostate gland is then freed from its surrounding structures by gentle dissection, and the urethra at the end of the prostate farthest from the bladder is isolated and divided. The bladder neck is freed from the prostate, and, once the prostate gland has been removed and the bladder neck has been closed sufficiently so that the size of its opening approximates the size of the urethral opening, the urethra and the bladder neck are stitched together. Once again, a Foley catheter is left in place postoperatively for about two weeks.

In each of the above described procedures, it is the attachment of the urethral stump to the bladder neck which is particularly difficult and complex. This difficulty is complicated by the tendency of the urethral stump to retract into adjacent tissue. As a result, considerable time and effort must be expended to re-expose the urethral stump and begin the re-anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating this procedure. In U.S. Pat. No. 5,591,179, issued to Edelstein, there is disclosed a suturing device including a shaft with portions defining an interior channel extending between a proximal and a distal end of the shaft. This channel includes a generally axial lumen which extends to the proximal end of the shaft and a generally transverse lumen which extends from the axial lumen distally outwardly to an exit hole at the outer surface of the shaft. A needle and suture can be back loaded into the transverse lumen of the channel while a generally non-compressible member can be movably mounted in the axial lumen of the channel. At the proximal end of the shaft a handle is provided with means operative to push the member distally through the lumen to deploy or expel the needle.

In U.S. Pat. No. 4,911,164, issued to Roth, there is disclosed a suture guide with a curved distal portion. The distal portion of the suture guide has a plurality of exterior axial grooves which can be used to align and guide a curved needle and attached suture. In order to drive the urethral stump to an accessible position, the device is provided with a plurality of outwardly extendable members which engage the lumen of the urethra. These members make it possible to push the urethral stump into approximation with the bladder neck.

In U.S. Pat. No. 5,047,039, issued to Avant et al., there is disclosed a surgical device for the ligation of a dorsal vein and subsequent anastomosis. This device contains a pair of enclosed needles each having an attached suture which needles may be driven from the shaft of the device into adjacent tissue.

In general, none of the devices disclosed in the prior art references above is simple to use or makes the anastomosis of the urethral stump to the bladder neck easier. As such, each surgical procedure using the prior art devices continues to be time consuming and to require great skill. Accordingly, the need exists for radical prostatectomy anastomosis devices which overcome the drawbacks of the prior art devices and which are quick and simple to use.

SUMMARY OF THE INVENTION

Apparatus and method for performing surgical anastomotic procedures are disclosed herein. The apparatus for performing the surgical anastomotic procedure includes a tubular sleeve defining an axial lumen therethrough, a positioning tube defining an axial lumen therethrough, an expansion assembly having a tubular body and an expandable tip operatively coupled to a distal end thereof, and an anchoring assembly. The positioning tube is preferably configured and adapted to be slidably received within the axial lumen of the tubular sleeve. The expandable tip of the expansion assembly preferably has a retracted position in which the expandable tip can pass through the axial lumen of the positioning tube and an expanded position in which the expandable tip can not pass through the axial lumen of the positioning tube. The anchoring assembly includes a flange member having a head portion and an expandable annular body integrally coupled to the head portion and a locking member defining a lumen therethrough. The flange member defines a passage extending through the head portion and the annular body. The locking member is preferably configured and adapted to radially deflect the expandable annular body upon insertion of the locking member within the passage of the annular body.

In a preferred embodiment of the disclosure, the expandable tip of the expansion assembly is or includes a balloon like structure which can be selectively inflated and deflated.

Preferably, the annular body of the anchoring assembly includes at least a pair of diametrically opposed longitudinal slots formed therein, wherein the annular body is expandable along the pair of longitudinal slots. It is contemplated that the longitudinal slots extend through a proximal terminal end of the annular body and terminate at a distance spaced from the head portion. In an alternative embodiment, it is envisioned that the annular body of the anchoring assembly include a plurality of longitudinal slots formed therein. In yet another alternative embodiment, it is envisioned that the annular body of the anchoring assembly include at least one helical slot extending through the terminal end of the annular body.

It is envisioned that the annular body of the anchoring assembly include a plurality of protuberances formed on an outer surface thereof. It is further envisioned that the head portion of the flange member of the anchoring assembly include a plurality of protuberances formed on a proximal surface thereof.

In one preferred embodiment of the present disclosure, it is contemplated that the annular body of the anchoring assembly has a first radius when not expanded and a second radius, larger than the first radius, when expanded. Preferably, the head portion of the flange member has a radius which is larger than the radius of the annular body.

The locking member preferably includes a cylindrical body having a distal end portion, wherein the cylindrical body has a radius which is larger than the first radius of the annular body and wherein the distal end portion of the cylindrical body tapers down to a radius which is smaller than the first radius of the annular body.

It is preferred that the head portion of the flange member of the anchoring assembly include a tapered distal surface in order to facilitate insertion and passage through a body lumen.

In accordance with the present disclosure, a proximal end of the locking member is configured and adapted to engage a distal end of the positioning tube.

In accordance with another embodiment of the present disclosure, it is envisioned that the head portion of the flange member has a radius which is larger than a radius of the lumen of the tubular sleeve. It is further contemplated that the head portion of the flange member has a radius which is smaller than an inner radius of the lumen of the tubular sleeve.

In accordance with the present disclosure it is preferred that the anchoring assembly is made from a bio-absorbable material.

A preferred method of performing a surgical anastomotic procedure, using the apparatus disclosed herein includes providing an apparatus as disclosed above, passing the apparatus through a body lumen and through an opening in a body vessel such that the head portion of the flange member of the anchoring assembly is positioned within the body vessel, advancing the expansion assembly through the positioning tube such that the expandable tip is within the body vessel, and expanding the expandable tip within the body vessel.

The method further includes the steps of withdrawing the tubular body of the expansion assembly to press the head portion of the flange member of the anchoring assembly against the body vessel and to approximate the body vessel within the body lumen until the annular body of the flange member of the anchoring assembly is positioned within a distal end of the body lumen, advancing the positioning tube through the tubular body to drive the locking member of the anchoring assembly into the annular body of the flange member and to deflect the annular body radially outward against the inner surface of the body lumen.

The method further includes the steps of retracting the expandable tip of the expansion assembly and withdrawing the tubular body. The method still further includes the step of positioning tube and the expansion assembly from the urethra.

It is envisioned that the surgical anastomosis is a radical prostatectomy. Accordingly, the radical prostatectomy includes the steps of removing the prostate gland from between the urethra and the bladder to define a urethral stump and a bladder neck.

In accordance with the present disclosure, an anchoring assembly for use in a surgical anastomosis procedure is provided including a flange member having a head portion and an expandable annular body integrally coupled to the head portion, the flange member defining a passage extending through the head portion and the annular body, and a locking member defining a lumen therethrough, the locking member being configured and adapted to radially deflect the expandable annular body upon insertion of the locking member within the passage of the annular body.

It is envisioned that the annular body of the anchoring assembly comprises at least a pair of diametrically opposed longitudinal slots formed therein, wherein the annular body is expandable along the pair of longitudinal slots. The annular body of the anchoring assembly has a first radius when not expanded and a second radius, larger than the first radius, when expanded. The head portion of the flange member has a radius which is larger than the first radius of the annular body.

The locking member includes a cylindrical body having a distal end portion, wherein the cylindrical body has a radius which is larger than the first radius of the annular body and wherein the distal end portion of the cylindrical body tapers down to a radius which is smaller than the first radius of the annular body. The longitudinal slots extend through a proximal end of the annular body and terminate at a distance spaced from the head portion.

These and other advantages and features of apparatus and method disclosed herein, will become apparent through reference to the following description of embodiments, the accompanying drawings and the claims.

BRIEF DESCRIPTION OF THE DRAWINGS

The accompanying drawings, which are incorporated in and constitute a part of this specification, illustrate embodiments of the disclosure and, together with the general description given above, and the detailed description of the embodiments given below, serve to explain the principles of the present disclosure.

DETAILED DESCRIPTION OF PREFERRED EMBODIMENTS

Preferred embodiments of the presently disclosed apparatus for performing an anastomosis will now be described in detail with reference to the drawing figures wherein like reference numerals identify similar or identical elements. In the drawings and in the description which follows, the term "proximal", as is traditional will refer to the end of the surgical device or instrument of the present disclosure which is closest to the operator, while the term "distal" will refer to the end of the device or instrument which is furthest from the operator.

Figure 1:
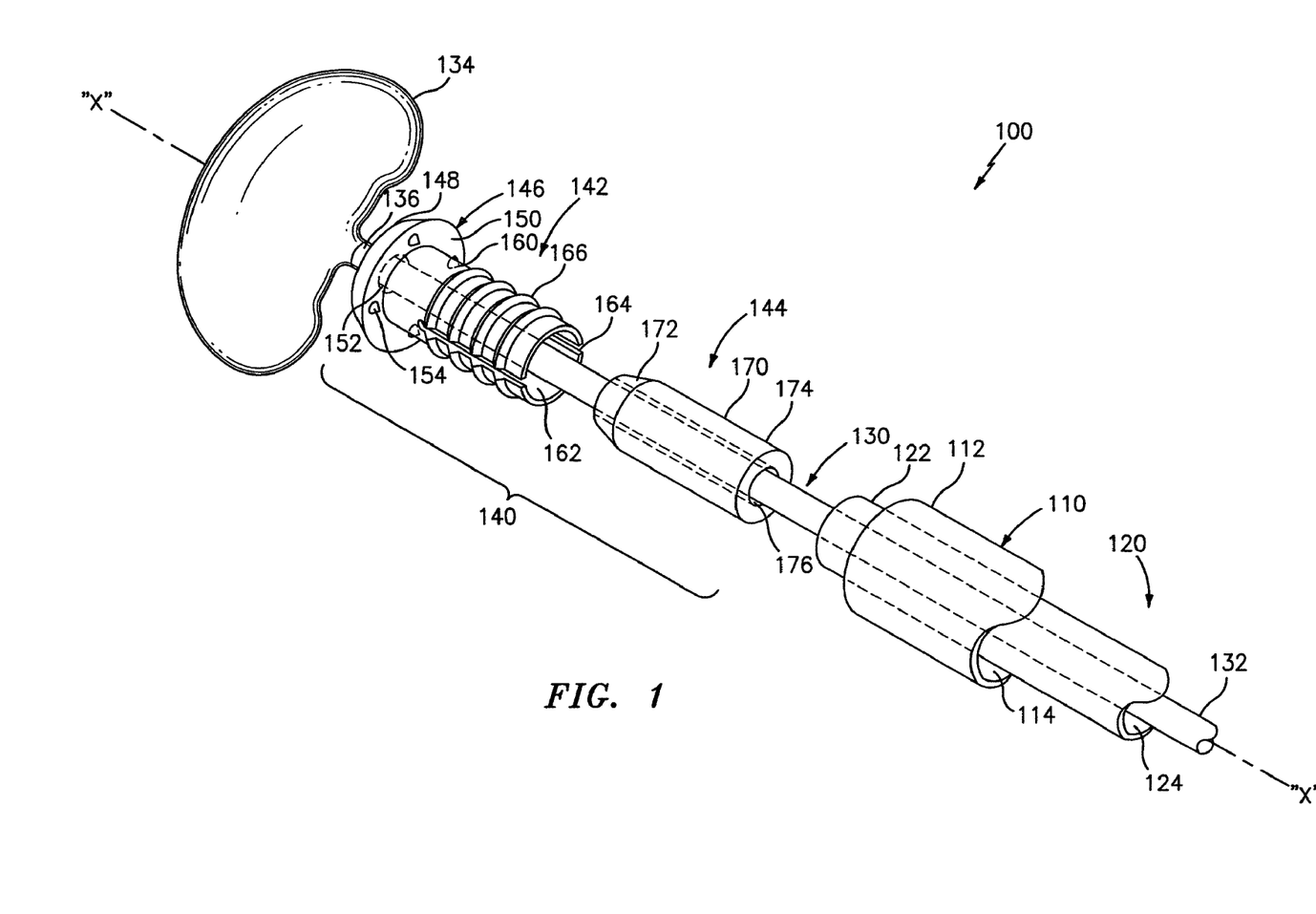
FIG. 1 is an exploded perspective view of an anastomosis apparatus in accordance with the present disclosure.
Figure 2:
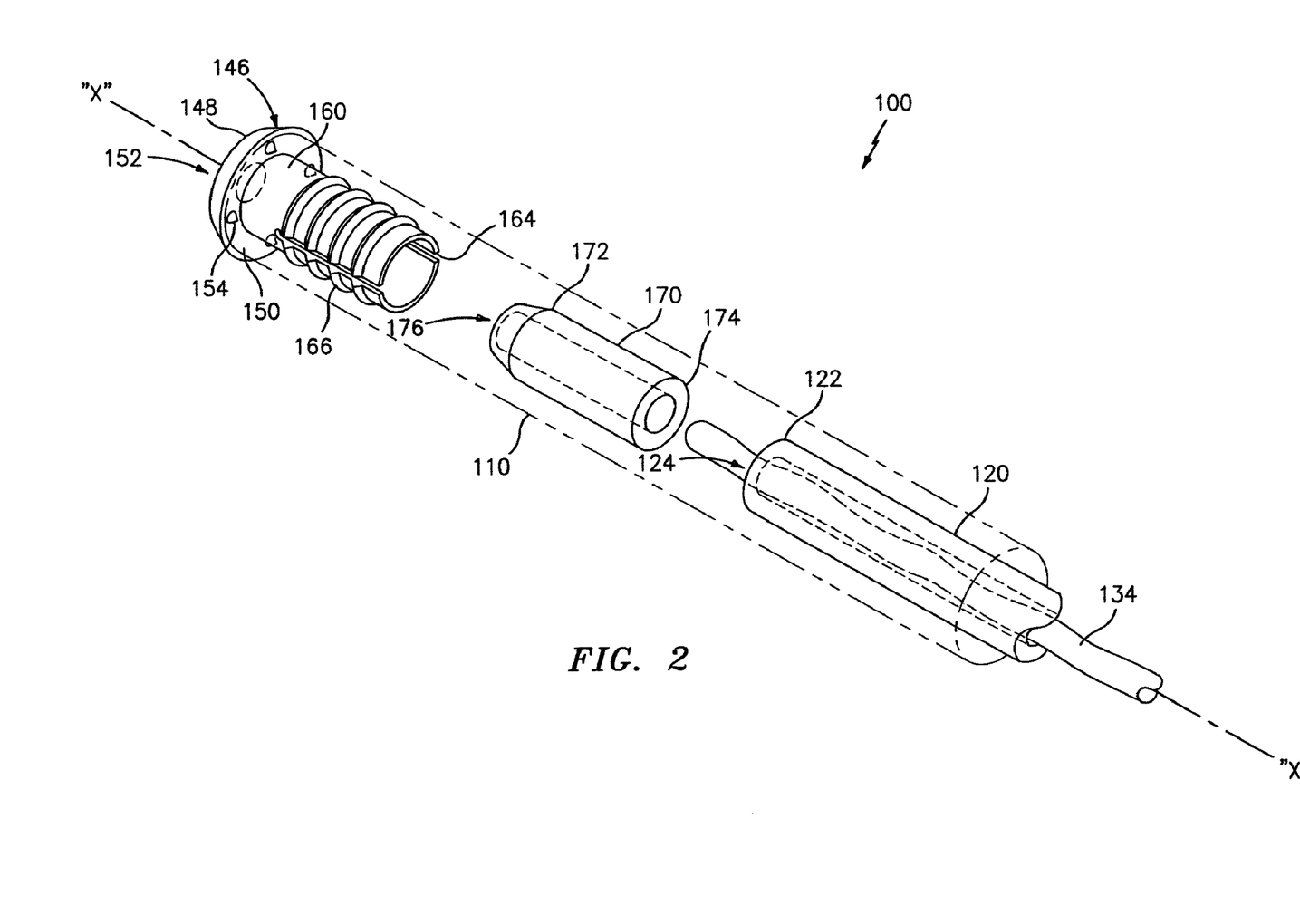
FIG. 2 is a perspective view of the apparatus of FIG. 1 shown in an insertion condition.

Referring to FIGS. 1 to 3C, and initially to FIGS. 1 and 2, an anastomosis apparatus in accordance with the present disclosure, is shown generally as reference numeral 100. Although apparatus 100 offers significant advantages to a radical prostatectomy procedure, it will be understood that the device is applicable for use in any anastomotic procedure where the end of a conduit is to be sutured or otherwise secured to a hollow body organ.

As seen in FIGS. 1 and 2, apparatus 100 includes a tubular sleeve 110, a positioning tube 120 slidably receivable within tubular sleeve 110, an expansion assembly 130 slidably receivable with positioning tube 120 and an anchoring assembly 140 in operative engagement with positioning tube 120.

Tubular sleeve 110 includes a distal end 112, a proximal end (not shown) and defines an axial lumen 114 extending therethrough. Axial lumen 114 of tubular sleeve 110 defines a central longitudinal axis "X".

Positioning tube 120 includes a distal end 122, a proximal end (not shown) and defines an axial lumen 124 extending therethrough. Preferably, positioning tube 120 is configured and adapted to be received within axial lumen 114 of tubular sleeve 110. In accordance with the present disclosure, it is preferred that axial lumen 124 of positioning tube 120 is co-axial with axial lumen 114 of tubular sleeve 110, however, it is envisioned that axial lumen 124 does not have to be co-axial with axial lumen 114. In particular, it is envisioned that positioning tube 120 can define an axial lumen 124 having a longitudinal axis which is spaced a distance from the longitudinal "X" axis of tubular sleeve 110.

In accordance with a preferred embodiment of the present disclosure, expansion assembly 130 includes a hollow inflation tube 132 having an inflatable balloon 134 coupled to a distal end 136 thereof. Inflation tube 132 is preferably configured and adapted to be received within axial lumen 124 of positioning tube 120. Balloon 134 has a deflated configuration for insertion and withdrawal of expansion assembly 130 into and out of positioning tube 120 and an inflated configuration for preventing the withdrawal of expansion assembly 130 from positioning tube 120. Balloon 134 is preferably fabricated from a medical grade polymer having suitable flexibility and structural integrity to withstand the forces associated with the inflation of balloon 134 and with the function of pressing against the inner surface of a body cavity.

While an inflation tube 132 and an inflatable balloon 134 have been disclosed, it is envisioned that any insertion tube having an expandable member operatively coupled to a distal end thereof can be used. In particular, it is contemplated that an expandable member be provided on an end of an insertion tube, which expandable member has a first position for insertion and passage through axial lumen 124 of positioning tube 120 and a second position which is preferably at least radially larger than axial lumen 124 of positioning tube 120. Accordingly, it is envisioned that expandable member can be pneumatic and/or mechanical.

Anchoring assembly 140 includes a flange member 142 and a locking member 144. Flange member 142 includes a head portion 146 having a distal end surface 148 and a proximal end surface 150. It is envisioned that distal end surface 148 of head portion 146 can be any shape including, arcuate, angled, chamfered, conical, blunt or beveled. Head portion 146 includes a through bore 152 formed therein. Through bore 152 is configured and adapted to permit passage of inflation tube 132 therethrough. Proximal end surface 150 of head portion 146 preferably includes a plurality of protuberances 154 projecting therefrom. In a preferred embodiment, protuberances 154 take the form of a plurality of pointed shapes configured to grip, dig into or engage an inner surface of the body cavity.

It is envisioned that head portion 146 can be sized to have a dimension which is either greater than or less than the inner diameter of tubular sleeve 110. If the dimension of head portion 146 is greater than the inner diameter of tubular sleeve 110, it is envisioned that the distal end of tubular sleeve 110 abuts against proximal end surface 150 of head portion 146 in order to distally advance anchoring assembly 140 through a body lumen and into the body cavity. If the dimension of head portion 146 is less than the inner diameter of tubular sleeve 110, it is envisioned that anchoring assembly 140 is completely retained within distal end 112 of tubular sleeve 110 for distal advancement of anchoring assembly 140 through the body lumen and into the body cavity.

Flange member 142 of anchoring assembly 140 further includes an annular body 160 extending from proximal end surface 150. Annular body 160 includes a central opening 162 extending therethrough. Annular body 160 includes a pair of diametrically opposed longitudinally oriented slots 164. While a pair of slots 164 has been disclosed, it is contemplated that any number of longitudinally oriented slots 164 can be formed in annular body 160. Preferably, slots 164 extend through the terminal end of annular body 160 and commence at a distance spaced from head portion 146. While slots 164 have been disclosed as being longitudinal, it is envisioned that slots 164 can angled relative to the longitudinal axis and/or helical about the longitudinal axis.

In accordance with a preferred embodiment of the present disclosure, annular body 160 is provided with a plurality of projections 166 formed along an outer surface thereof. It is envisioned that projections 166 may be similar to protuberances 154 formed on proximal end surface 150 of head portion 146 in order to grip, dig into and engage an inner surface of the body lumen. It is also envisioned that projections 166 can also form a series of circumferential undulations such as a series of threads, rings or ribs.

Locking member 144 includes a body portion 170 having a distal end 172, a proximal end 174 and defining a lumen 176 extending therethrough. In accordance with the present disclosure, lumen 176 of locking member 144 is configured and adapted to permit passage of inflation tube 132 therethrough. Body portion 170 has an outer diameter which is larger than an inner diameter of annular body 160. Distal end 172 of locking member 144 is angled to terminate in a distal tip which is sized to be received within central opening 162 of annular body 160, wherein distal end 172 defines a cramming surface.

Preferably, locking member 144 is placed within tubular sleeve 110 such that proximal end 174 is adjacent distal end 122 of positioning tube 120 and next at least annular body 160 of flange member 142 is placed within tubular sleeve 110, distally of locking member 144.

As will be discussed in greater detail below, as locking member 144 is advanced distally through central opening 162 of annular body 160, by a distal advancement of positioning tube 120, distal end 172 of locking member 144 will cause a proximal end of annular body 160 to deflect radially outward. The more locking member 144 is advanced distally the more annular body 160 deflects radially.

Various different materials may be used to fabricate flange member 142 and locking member 144 of anchoring assembly 140. In particular, anchoring assembly 140 should preferably be made of materials having acceptable properties including biocompatibility, pull strength, longitudinal and column strength and bending flexibility. Some of the preferred materials may include various plastics, referred to as polymers, including nylon, polyethylene, polyurethanes or PET. It is further contemplated that anchoring assembly 140 is made from a medical grade bio-absorbable material, such as, for example, polyglycolic acid (PGA) and/or polylactic acid (PLA). Preferably, if a bio-absorbable material is used it is preferred that anchoring assembly 140 have sufficient endurance to retain its structural integrity for at least the period required for a natural growth joining of tissue portions for an anastomotic procedure. For example, it is preferred that anchoring assembly 140 have sufficient structural integrity for at least two weeks in the anastomosis of a bladder to a urethra in a radical prostatectomy procedure.

A preferred method of use and operation of anastomosis apparatus 100 in performing a radical prostatectomy anastomosis will now be described in greater detail with reference to FIGS. 1-3C and in particular with reference to FIGS. 3A-3C. Apparatus 100 can be used in either the retropubic or the perineal prostatectomy approaches. With the prostate removed, the bladder neck "N" of the bladder "B" is first reconstructed by everting the inner mucosal lining of bladder "B" and suturing it down to the outer wall of bladder "B", using known surgical techniques. Likewise, urethral stump "S" of urethra "U" is reconstructed by everting the inner mucosal lining of urethral stump "S" and suturing it down to the outer wall of urethra "U", using known surgical techniques.

Apparatus 100 is assembled as described above. In particular, apparatus 100 is preferably assembled such that at least annular body 160 of flange member 142 of anchoring assembly 140 is inserted within distal end 112 of tubular sleeve 110, locking member 144 is inserted through tubular body 110 such that distal end 172 of locking member 144 contacts a proximal end of annular body 160 and positioning tube 120 is inserted through tubular body 110 such that distal end 122 of positioning tube 120 contacts a proximal surface of locking member 144.

With bladder neck "N" reconstructed, bladder neck "N" is sized to properly accommodate head portion 146 of flange member 142, through bladder neck "N", within bladder "B" using a standard tennis racket type closure (i.e., the opening of the bladder neck constituting the head of the tennis racket and a radial incision extending from the bladder neck constituting the handle portion of the tennis racket). Most preferably, bladder neck "N" is sized to be approximately 7-8 mm in diameter.

Figure 3A:
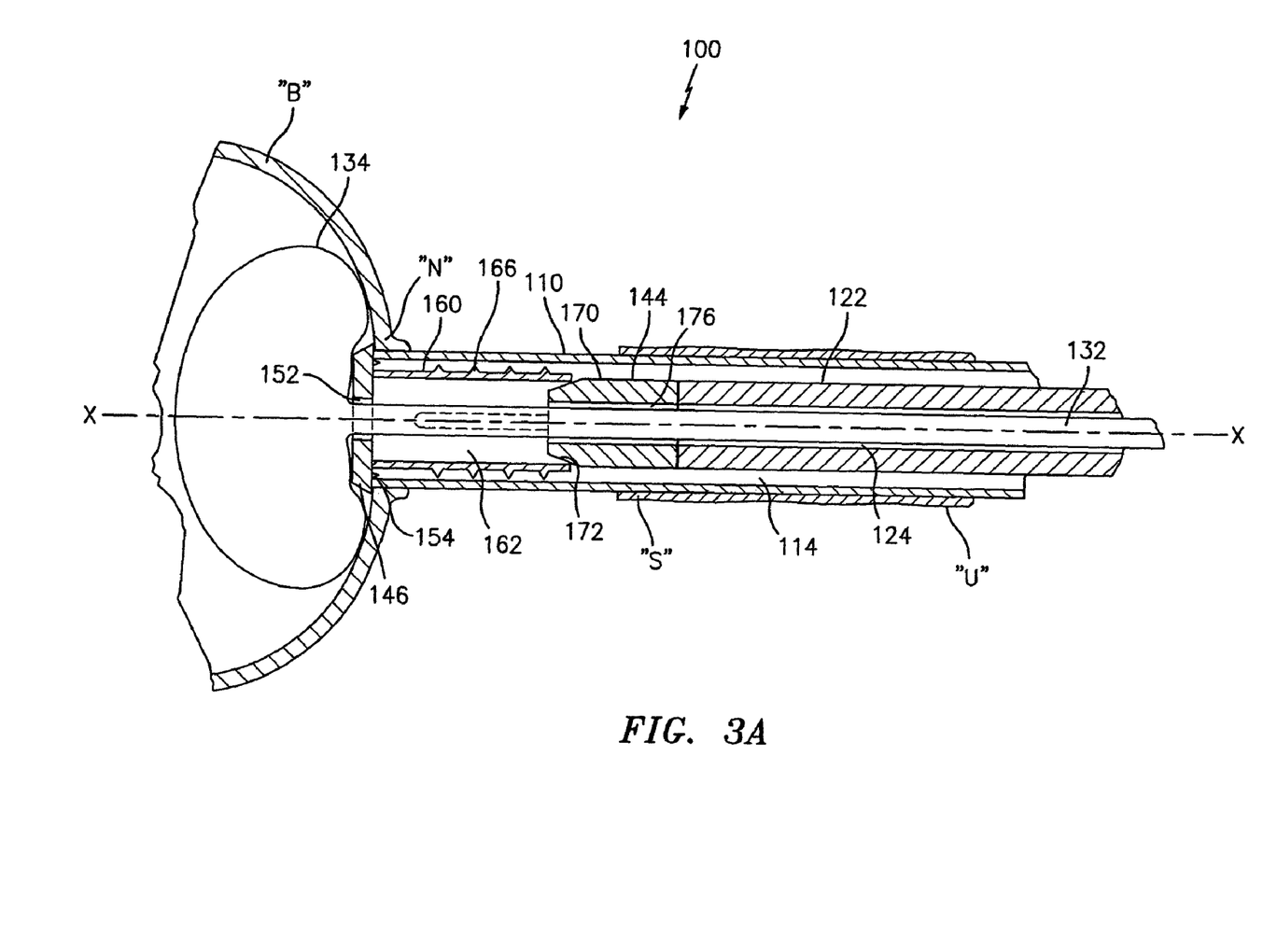
FIG. 3A is a cross-sectional side elevational view of the apparatus of FIG. 1 shown passing through a body lumen and positioned within a body cavity.
Figure 3B:
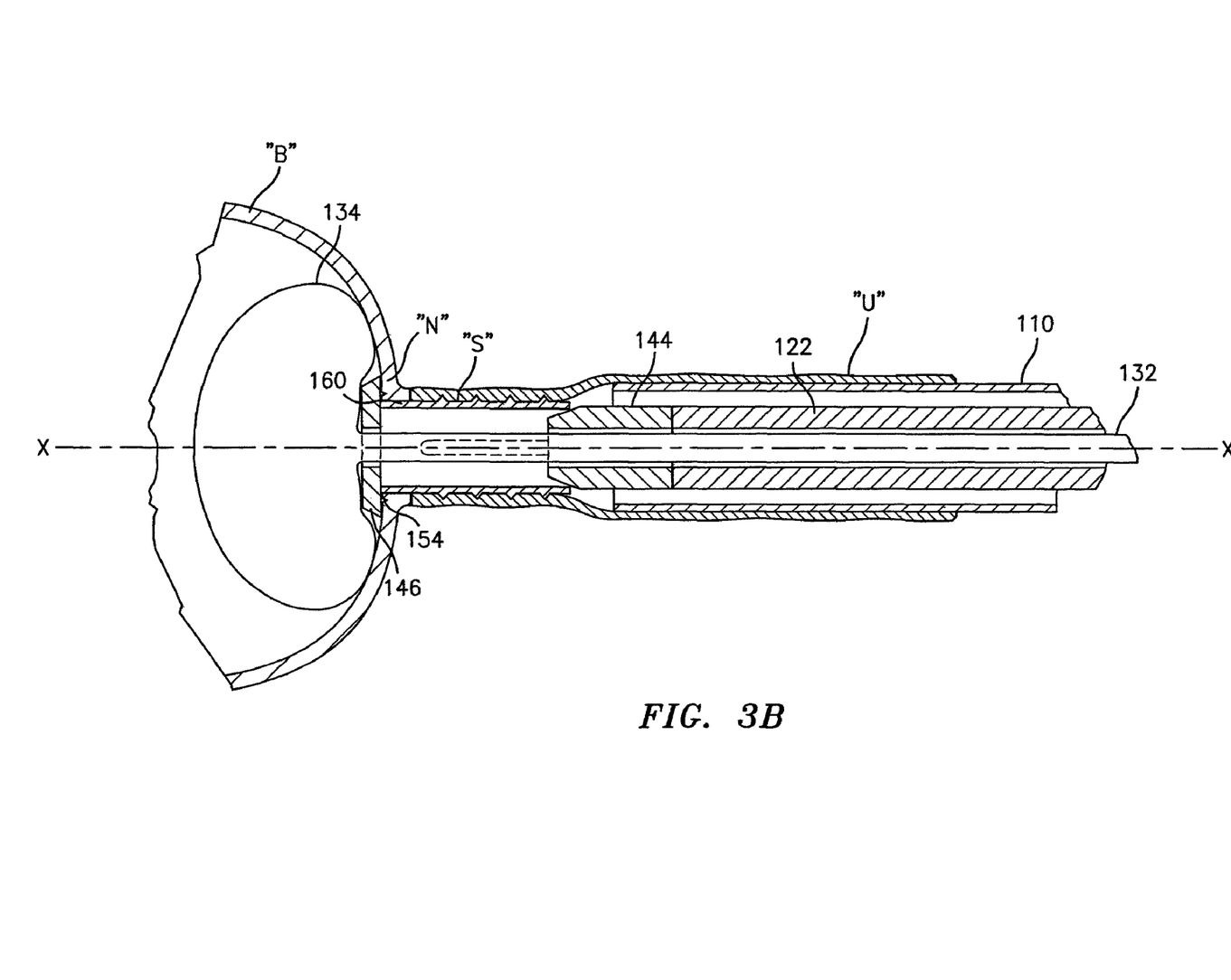
FIG. 3B is a cross-sectional side elevational view of the apparatus of FIG. 1 shown with the body lumen in apposition with the body cavity.

As seen in FIG. 3A, head portion 146 of flange member 142 is sized to be larger than the inner diameter of tubular sleeve 110. Accordingly, distal end 112 of tubular sleeve 110 will abut against proximal end surface 150 of head portion 146 during insertion.

With bladder neck "N" reconstructed, anchor assembly 140 is moved into position such that head portion 146 of flange member 142 is located within bladder "B" by advancing tubular sleeve 110 trans-urethrally through urethra "U" until distal end 112 of tubular sleeve 110, including head portion 146 of flange member 142, extends out of urethra "U" and into bladder "B", as seen in FIG. 3A. In particular, as seen in FIG. 3A, tubular sleeve 110 is advanced a distance such that head portion 146 of flange member 142 is located entirely within bladder "B". With tubular sleeve 110 and flange member 142 so positioned, expansion assembly 130 is passed through axial lumen 124 of positioning tube 120, through lumen 176 of locking member 144, through central opening 162 and through bore 152 of flange member 142 until balloon 134 is disposed within bladder "B".

With balloon 134 disposed within bladder "B", a fluid from a fluid source (not shown) is injected into balloon 134 through inflation tube 132 in order to inflate balloon 134. As seen in FIG. 3B, with balloon 134 inflated, tubular body 110 is partially withdrawn in order for bladder neck "N" to close down around annular body 160 and in order for protuberances 154 to engage the inner surface of bladder neck "N". Inflation tube 132 is then withdrawn in a proximal direction in order for inflated balloon 132 to contact and press against distal end 148 of flange member 142, thereby further driving protuberances 154 into bladder neck "N", and in order to approximate bladder neck "N" to urethral stump "S".

While holding inflation balloon 134 stationary, positioning tube 120 is advanced distally in order to drive locking member 144 forward. By driving locking member 144 forward, distal end 172 of locking member 144 enters central opening 162 of annular body 160. Further advancement of positioning tube 120 causes the proximal end of annular body 160 to ride or be cammed along distal end 172 to thereby deflect the proximal end of annular body 160 radially outward along longitudinally oriented slots 164 (see FIG. 3C). As the proximal end of annular body 160 gets deflected radially outward, protuberances 166 formed on an outer surface thereof engage the inner surface of urethral stump "S" thereby maintaining bladder neck "N" approximated with urethral stump "S". Preferably, locking member 144 is distally advanced until distal end 172 is frictionally secured within central opening 162 of annular body 160.

Figure 3C:
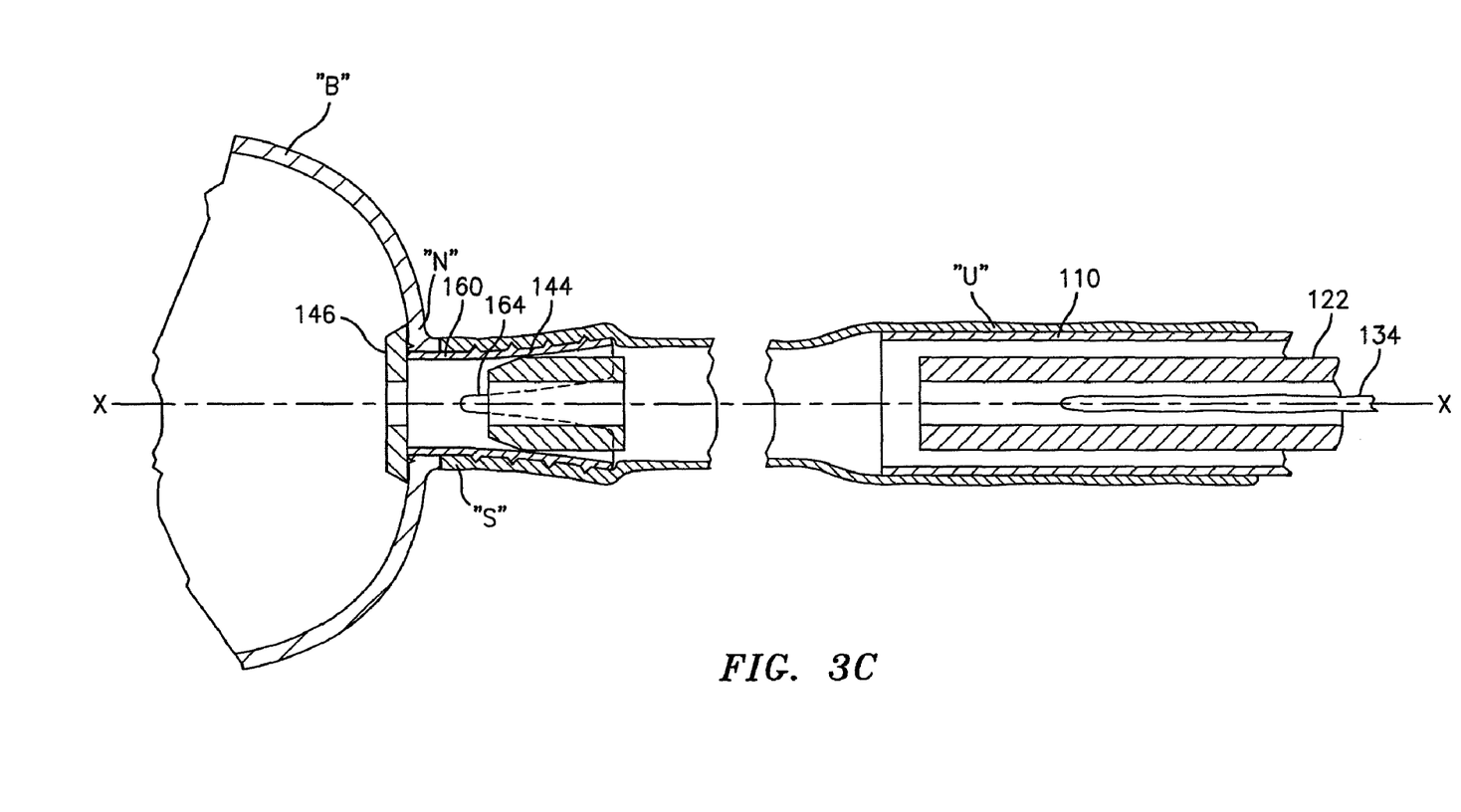
FIG. 3C is a cross-sectional side elevational view showing the placement of an anchor of the apparatus of FIG. 1 in position between the body lumen and the body cavity.

As seen in FIG. 3C, with locking member 144 secured within annular body 160, balloon 134 is deflated and tubular sleeve 110, positioning tube 120 and expansion assembly 130 are withdrawn proximally through urethra "U".

The expandable anchor for engaging a body vessel may comprise any expandable structure, including those disclosed in certain embodiments of the following PCT Applications, all filed on an even date herewith: application entitled method and apparatus for anastomosis including an anchoring sleeve, invented by Scott Manzo; method and apparatus for anastomosis including an anchor for engaging a body vessel and deployable sutures, invented by Scott Manzo; method and apparatus for anastomosis including annular joining member, invented by Scott Manzo; method and apparatus for anastomosis including an expandable member, invented by Russell Heinrich and Scott Manzo; method and apparatus for anastomosis including an expandable member, invented by Russell Heinrich and Scott Manzo; method and apparatus for anastomosis including an anchoring sleeve, invented by Scott Manzo; method and apparatus for radical prostatectomy anastomosis, invented by Scott Manzo; the disclosures of which are all hereby incorporated by reference herein, in their entirety.

The joining member for joining body vessels may comprise any joining member, including those disclosed in certain embodiments of the following PCT Applications, all filed on an even date herewith: application entitled method and apparatus for anastomosis including an anchoring sleeve, invented by Scott Manzo; method and apparatus for anastomosis including an anchor for engaging a body vessel and deployable sutures, invented by Scott Manzo; method and apparatus for anastomosis including an anchor for engaging a body vessel and deployable sutures, invented by Scott Manzo; method and apparatus for anastomosis including an anchoring sleeve, invented by Scott Manzo; method and apparatus for anastomosis including annular joining member, invented by Scott Manzo; method and apparatus for anastomosis including an expandable member, invented by Russell Heinrich and Scott Manzo; method and apparatus for anastomosis including an expandable member, invented by Russell Heinrich and Scott Manzo; method and apparatus for anastomosis including an anchoring sleeve, invented by Scott Manzo; method and apparatus for radical prostatectomy anastomosis, invented by Scott Manzo; the disclosures of which are all hereby incorporated by reference herein, in their entirety.

The methods and apparatus disclosed herein may be used for approximating and/or joining the urethra and bladder, intestinal portions of the body, blood vessels or any other body vessels.

Although the illustrative embodiments of the present disclosure have been described herein with reference to the accompanying drawings, it is to be understood that the disclosure is not limited to these embodiments, and that various other changes and modifications may be affected therein by one skilled in the art without departing from the scope or spirit of the disclosure. All such changes and modifications are intended to be included within the scope of the appended claims.

What is claimed is:

1. A method for performing a surgical anastomosis, comprising the steps of:
   providing an apparatus for performing the surgical anastomosis, the apparatus comprising:
   a positioning tube defining a lumen therethrough,
   an expansion assembly having a tubular body and an expandable tip operatively coupled to a distal end thereof, the expandable tip having a first condition in which the expandable tip is configured for passage through the lumen of the positioning tube and a second condition in which the expandable tip is prevented from passage through the lumen of the positioning tube; and
   an anchoring assembly including:
   a flange member having an expandable annular body and a head portion integrally coupled to the expandable annular body and protruding radially therefrom, the annular body defining a passage therethrough for passage of the tubular body therethrough, the passage extending through the head portion and the annular body; and
   a locking member arranged to be received in the passage of the flange member, the locking member defining a lumen therethrough, the locking member being configured and adapted to radially deflect the expandable annular body upon insertion of the locking member within the passage of the annular body and to maintain the expandable annular body in the radially deflected configuration when the locking member is received in the passage of the flange member, the locking member being configured for operable engagement with the positioning tube such that the positioning tube is advanceable in a distal direction to drive the locking member distally with respect to the annular body, and the locking member being selectively releasable and separable from the positioning tube;
   passing the apparatus through a body lumen and through an opening in a body vessel such that the head portion of the flange member of the anchoring assembly is positioned within the body vessel;
   advancing the expansion assembly through the passage of the annular body of the anchoring assembly and into the body vessel such that the expandable tip is within the body vessel;
   expanding the expandable tip within the body vessel;
   withdrawing the tubular body of the expansion assembly to press the head portion of the flange member of the anchoring assembly against the body vessel and to approximate the body vessel with the body lumen until the annular body of the flange member of the anchoring assembly is positioned within a distal end of the body lumen;
   advancing the positioning tube through the body lumen;
   driving and securing the discrete locking member of the anchoring assembly into the passage of the annular body of the flange member, deflecting the annular body radially outward in a proximal direction away from the head portion and against the inner surface of the body lumen, maintaining the expandable annular body in the radially deflected configuration with said discrete locking member; and
   withdrawing the positioning tube from the body lumen thereby leaving the locking member retained in the annular body of the flange member.

2. The method according to claim 1, wherein the surgical anastomosis is a radical prostatectomy.

3. The method according to claim 2, wherein the radical prostatectomy includes the steps of removing the prostate gland from between the urethra and the bladder to define a urethral stump and a bladder neck.

4. The method according to claim 1, wherein the expandable tip of the expansion assembly is a balloon, wherein the step of expanding the expandable tip includes inflating the balloon.

5. A method for performing a surgical anastomosis, comprising the steps of:
   providing an apparatus for performing the surgical anastomosis, the apparatus comprising:
   a tubular sleeve defining a lumen therethrough;
   a positioning tube defining a lumen therethrough, the positioning tube being configured and adapted to be slidably received within the axial lumen of the tubular sleeve;
   an expansion assembly having a tubular body and an expandable tip operatively coupled to a distal end thereof, the expandable tip having a first condition in which the expandable tip is configured for passage through the lumen of the positioning tube and a second condition in which the expandable tip is prevented from passage through the lumen of the positioning tube; and an anchoring assembly including:

a flange member having an expandable annular body and a head portion integrally coupled to the expandable annular body and protruding radially therefrom, the annular body defining a passage therethrough for passage of the tubular body therethrough, the passage extending through the head portion and the annular body; and a locking member arranged to be received in the passage of the flange member, the locking member defining a lumen therethrough, the locking member being configured and adapted to radially deflect the expandable annular body upon insertion of the locking member within the passage of the annular body and to maintain the expandable annular body in the radially deflected configuration when the locking member is received in the passage of the flange member, the locking member being configured for operable engagement with the positioning tube such that the positioning tube is advanceable in a distal direction to drive the locking member distally with respect to the annular body, and the locking member being selectively releasable and separable from the positioning tube;

passing the apparatus through a body lumen and through an opening in a body vessel such that the head portion of the flange member of the anchoring assembly is positioned within the body vessel;

advancing the expansion assembly through the positioning tube such that the expandable tip is within the body vessel;

expanding the expandable tip within the body vessel;

withdrawing the tubular body of the expansion assembly to press the head portion of the flange member of the anchoring assembly against the body vessel and to approximate the body vessel with the body lumen until the annular body of the flange member of the anchoring assembly is positioned within a distal end of the body lumen;

advancing the positioning tube through the tubular body;

driving and securing the discrete locking member of the anchoring assembly into the annular body of the flange member, deflecting the annular body radially outward in a proximal direction away from the head portion and against the inner surface of the body lumen, maintaining the expandable annular body in the radially deflected configuration with said discrete locking member; and releasing the locking member from the positioning tube by withdrawing the positioning tube from the body lumen to separate the positioning tube from the locking member; and thereafter maintaining the discrete locking member of the anchoring assembly within the annular body of the flange member.

6. The method according to claim 5, further comprising the step of retracting the expandable tip of the expansion assembly.

7. The method according to claim 6, further comprising the step of:

withdrawing the tubular body and the expansion assembly from the body lumen.

8. The method according to claim 7, wherein the surgical anastomosis is a radical prostatectomy.

9. The method according to claim 8, wherein the radical prostatectomy includes the steps of removing the prostate gland from between the urethra and the bladder to define a urethral stump and a bladder neck.

10. An apparatus for performing a surgical anastomosis, comprising:

a tubular sleeve defining a lumen therethrough;

a positioning tube defining a lumen therethrough, the positioning tube being configured and adapted to be slidably received within the axial lumen of the tubular sleeve;

an expansion assembly having a tubular body and an expandable tip operatively coupled to a distal end thereof, the expandable tip having a first condition in which the expandable tip is configured for passage through the lumen of the positioning tube and a second condition in which the expandable tip is prevented from passage through the lumen of the positioning tube; and an anchoring assembly, including:

a flange member having an expandable annular body and a head portion integrally coupled to the expandable annular body and protruding radially therefrom, the annular body defining a passage therethrough for passage of the tubular body therethrough, the passage extending through the head portion and the annular body; and a locking member configured and dimensioned to be received in the passage of the annular body, the locking member defining a lumen therethrough, the locking member being configured for operable engagement with the positioning tube such that the positioning tube is movable in a distal direction to drive the locking member distally with respect to the annular body, and the locking member being selectively releasable and separable from the positioning tube;

wherein movement of the locking member into the passage of the annular body induces radial expansion of the annular body of the flange member between an unexpanded configuration and a radially expanded configuration in which the annular body flares radially outward in a proximal direction away from the head portion, and wherein the locking member is maintained in the annular body to maintain the annular body in the expanded configuration when the locking member is released from the positioning tube and separated from the positioning tube.

11. The apparatus according to claim 10, wherein the expandable tip of the expansion assembly is a balloon.

12. The apparatus according to claim 10, wherein the annular body of the anchoring assembly comprises at least a pair of diametrically opposed longitudinal slots formed therein, wherein the annular body is expandable along the pair of longitudinal slots.

13. The apparatus according to claim 12, wherein the annular body of the anchoring assembly includes a plurality of protuberances formed on an outer surface thereof.

14. The apparatus according to claim 12, wherein the annular body of the anchoring assembly has a first radius when not expanded and a second radius, larger than the first radius, when expanded.

15. The apparatus according to claim 14, wherein the head portion of the flange member has a radius which is larger than the first radius of the annular body.

16. The apparatus according to claim 15, wherein the locking member includes a cylindrical body having a distal end portion, wherein the cylindrical body has a radius which is larger than the first radius of the annular body and wherein the distal end portion of the cylindrical body tapers to a radius which is smaller than the first radius of the annular body.

17. The apparatus according to claim 12, wherein the longitudinal slots extend through a proximal terminal end of the annular body and terminate at a distance spaced from the head portion.

18. The apparatus according to claim 10, wherein the head portion defines proximal and distal end surfaces, the proximal end surface including a plurality of protuberances formed thereon and extending proximally therefrom.

19. The apparatus according to claim 10, wherein the head portion includes a tapered distal surface.

20. The apparatus according to claim 10, wherein the annular body of the anchoring assembly comprises a plurality of longitudinal slots formed therein.

21. The apparatus according to claim 10, wherein a proximal end of the locking member is configured and adapted to engage a distal end of the positioning tube.

22. The apparatus according to claim 10, wherein the head portion of the flange member has a radius which is larger than a radius of the lumen of the tubular sleeve.

23. The apparatus according to claim 10, wherein the head portion of the flange member has a radius which is smaller than an inner radius of the lumen of the tubular sleeve.

24. The apparatus according to claim 10, wherein the anchoring assembly is made from a bio-absorbable material.

\* \* \* \* \*